United States Patent [19]

Mirviss

[11] Patent Number: 4,845,271

[45] Date of Patent: Jul. 4, 1989

[54] PROCESS FOR THE PREPARATION OF OMEGA-UNSATURATED CARBOXYLIC ACIDS

[75] Inventor: Stanley B. Mirviss, Stamford, Conn.

[73] Assignee: Akzo America Inc., New York, N.Y.

[21] Appl. No.: 7,041

[22] Filed: Jan. 27, 1987

[51] Int. Cl.$^4$ .................................................. C09F 5/00
[52] U.S. Cl. ................................ 260/405.5; 260/408; 260/413; 562/602
[58] Field of Search ..................... 260/413, 408, 405.5; 562/602

[56] References Cited

U.S. PATENT DOCUMENTS

| 2,921,939 | 1/1960 | Ramsden ............................... 260/413 |
| 4,144,397 | 3/1979 | Mathews et al. ................ 562/602 X |

FOREIGN PATENT DOCUMENTS 61-548  4/1985  Japan .................................... 260/413

OTHER PUBLICATIONS

Barraud, A. et al., *J. Colloid Interface Sci.*, 1977, 62, 509.
Barraud, A. et al., *Thin Solid Films*, 1980, 68, 91.
Barraud, A. et al., *Solid State Tech.*, 1979, Aug. 120.
Fariss, G. et al., *Thin Solid Films*, 1983, 99, 305.
Peterson, I. R. et al., *Thin Solid Films*, 1983, 109, 371.
Stenhagen, E., *Arkiv Kemi, Min. O. Geol.*, 1949, 1 (13), 99.
Bowman, R. et al., *J. Chem. Soc.*, 1952, 3945.
Sisido, K. et al., *J. Org. Chem.*, 1962, 27, 3722.
Hunig, S. et al., *Ber.* 1962, 95, 2498.
Gunstone et al., *Chem. Phys. Lipids*, 1967, 1, 209.
Huisgen, R. et al., *Tetrahedron*, 1959, 6, 253.
Smissman, E. et al., *J. Org. Chem.*, 1964, 29, 3517.
Joycelyn, P. et al., *J. Org. Chem.*, 1953, 132.
*Organic Synthesis*, Collect., vol. I, Wiley, New York, N.Y., 1941, p. 29.
Bergbreiter, D. et al., *J. Org. Chem.*, 1975, 40, 779.
Baer, T. et al., *Tetrahedron Letters*, 1976, 4697.

*Primary Examiner*—Werren B. Lone
*Attorney, Agent, or Firm*—Richard P. Fennelly; Louis A. Morris

[57] ABSTRACT

An improved method for the synthesis of omega-unsaturated carboxylic acids is disclosed which precludes double bond migration or hydrogenation in order to prepare a high purity product necessary for high resolution in forming a resist by electron beam microlithography. This result can be obtained by a coupling reaction between a Grignard reagent of an unsaturated organochloride compound as defined in the application with a halo magnesium salt of a long chain organic acid.

15 Claims, No Drawings

PROCESS FOR THE PREPARATION OF OMEGA-UNSATURATED CARBOXYLIC ACIDS

The present invention relates to an improved method for the synthesis of omega-unsaturated carboxylic acids which method provides higher yields and precludes double bond migration or hydrogenation.

BACKGROUND OF THE PRESENT INVENTION

Omega-tricosenoic acid (22-tricosenoic acid) has been of interest for ultra thin layer photoresists (see Barraud, A. et al., *J. Colloid Interface Sci.*, 1977, 62, 509; Barraud, A. et al., *Thin Solid Films*, 1980, 68, 91; Barraud et al., *Solid State Tech.*, 1979, August, 120; Fariss, G. et al., *Thin Solid Films*, 1983, 99, 305; and Peterson, I. R. et al., *Thin Solid Films*, 1983, 109, 371. The synthesis routes in the literature for this compound involve many steps (see Barraud, A. et al., *J. Colloid Interface Sci.*, 1977, 62, 509; Stenhagen, E., *Arkiv Kemi, Min. O. Geol.*, 1949, 1, (13), 99; and Bowman, R. et al., *J. Chem. Soc.*, 1952, 3945. The products are not adequately pure for photoresists because of the small amounts of double bond migration and hydrogenation that occur in the final synthesis step, i.e., the Wolff-Kischner reduction (or the Huang-Minlon Modification) of the intermediate omega-unsaturated keto acids. These side reactions have been noted before (see Sisido, K. et al., *J. Org. Chem.* 1962, 27, 3722). Even when milder reduction conditions (Hunig, S. et al., *Ber.* 1962, 95, 2498) or the sodium borohydride reduction of the tosyl hydrazone of the keto group (Gunstone et al., *Chem. Phys. Lipids*, 1967, 1, 209) are used, small amounts of these side reactions occur.

The presence of trace amounts of by-products with internal double bonds, no double bonds or shorter or longer chain lengths interfere with the x-ray or electron beam polymerization of the terminal double bond. Thus, high purity is necessary for high resolution in the resist by electron beam microlithography (Barraud et al., *Solid State Tech.*, 1979, August, 120).

BRIEF SUMMARY OF THE INVENTION

An improved method for the synthesis of omega-unsaturated carboxylic acids has been developed which precludes double bond migration or hydrogenation. It has been found that this result can be obtained by a coupling reaction between a Grignard reagent of an unsaturated organochloride compound and the halo magnesium salt of an organic acid.

DETAILED DESCRIPTION OF THE PRESENT INVENTION

The process of the present invention can be illustrated in the following four equations:

$$Halo^1(CH_2)_{n_1}CO_2H + C_1\text{--}C_4MgHalo^2 \xrightarrow{\text{ether solvent}} \quad 1.$$

$$Halo^1(CH_2)_{n_1}CO_2MgHalo^2 + C_1\text{--}C_4 \text{ Alkane}$$
$$II$$

$$CH_2=CH(CH_2)_{n_2}OH + SOHalo_2^3 \xrightarrow{\text{catalyst}} \quad 2.$$

$$CH_2=CH(CH_2)_{n_2}Halo^3$$
$$III$$

$$III + Mg \xrightarrow{\text{ether solvent}} CH_2=CH(CH_2)_{n_2}MgHalo^3 \quad 3.$$
$$IV$$

$$II + IV \xrightarrow{Li_2Cu(Halo^4)_4}{\text{ether solvent}} CH_2=CH(CH_2)_{n_1+n_2}CO_2H \quad 4.$$
$$V$$

wherein
 Halo$^1$ is preferably Br though I and Cl can also be used, the latter being less preferred;
 Halo$^2$ is preferably Br though I or Cl can also be used;
 Halo$^3$ is preferably Cl though Br and I can also be used;
 Halo$^4$ is preferably Cl though Br can also be used; and
 n, 1 is an integer of from 4–20 inclusive, preferably 8–14 and n$_2$ is an integer ranging from 3–20 inclusive and preferably 7–14. In step 1., there is preferably used a lower alkyl magnesium halide of from $C_1$–$C_4$ carbon and preferably $C_1$–$C_2$ carbon. The lower chain length alkanes are gases which can be evolved during the course of the reaction to limit by-products retention in the product. The ether solvent is preferably tetrahydrofuran (THF) though dioxane, diethyl ether and dimethyl ether of ethylene glycol as well as other such glycol ethers and dialkyl ethers can also be used. The catalyst in step 2. is preferably pyridine which is used in trace catalytic amounts though other tertiary amines, such as triethyl amine, can also be used. The reaction can also be conducted without a catalyst, albeit not as readily.

The present invention will be further discussed in connection with a preferred embodiment wherein Halo$^1$ and Halo$^2$ are Br, Halo$^3$ and Halo$^4$ are Cl, and n$_1$ is 11, and n$_2$ is 9, the $C_1$–$C_4$ alkyl group in step 1. is ethyl, the ether solvent is tetrahydrofuran (THF) and the catalyst is pyridine as outlined in the following equations:

$$Br(CH_2)_{11}CO_2H + C_2H_5MgBr \xrightarrow{THF} \quad 5.$$
$$VI$$

$$Br(CH_2)_{11}CO_2MgBr + C_2H_6$$
$$VII$$

$$CH_2=CH(CH_2)_9OH + SOCl_2 \xrightarrow{C_5H_5N} \quad 6.$$

$$CH_2=CH(CH_2)_9Cl + SO_2 + HCl$$
$$VIII$$

$$VIII + Mg \xrightarrow{THF} CH_2=CH(CH_2)_9MgCl \quad 7.$$
$$IX$$

$$VII + IX \xrightarrow{Li_2CuCl_4} CH_2=CH(CH_2)_{20}CO_2H \quad 8.$$
$$X$$

The omega-bromododecanoic acid VI was prepared by the reaction of cyclododecanone with peroxytrifluoroacetic acid to form the lactone (see Huisgen, R. et al., *Tetrahedron*, 1959, 6, 253), lactone hydrolysis with dilute sodium hydroxide to produce 12-hydroxydodecanoic acid (see Smissman, E. et al., *J. Org. Chem.*, 1964, 29, 3517), and then the conversion of the hydroxy acid to 12-bromododecanoic acid with 48% hydrobromic acid in the presence of sulfuric acid (see Jocelyn, P. et el., *J. Org. Chem.*, 1953, 132; *Organic Synthesis, Collect. Vol. I*, Wiley, New York, N.Y., 1941, p. 29). The product after recrystallization showed no evidence of 11-bromododecanoic acid contaminants by NMR and GC and the product (VI) had properties identical with that discussed in the literature.

The compound identified as VII was prepared by adding an excess of a Grignard reagent (an alkylmagnesium halide such as EtMgBr) in an ether solvent such as diethyl ether or tetrahydrofuran to a solution of VI in an ether solvent, preferably at such a rate to allow the temperature to be maintained at a low point, i.e., from about −20° C. to about 30° C. The reaction can be continued until there is no further evolution of gas, indicating completion of the reaction.

The compound identified as VIII was prepared in 91% yield from 10-undecenyl alcohol and thionyl chloride with properties identical to those reported for VIII made by another route (see Bergbreiter, D. et al. *J. Org. Chem.*, 1975, 40, 779).

The thionyl chloride was added slowly to a solution of the corresponding alcohol over a period of time sufficient to allow maintenance of temperature at between about 10° C. and about 100° C. After addition, the reaction was heated at an elevated temperature ranging from about 40° C. to about 100° C. for a period of time sufficient to bring the reaction to the desired completion. The product can be, and preferably is, washed and isolated.

Compound IX was prepared by refluxing compound VIII with magnesium in the presence of a dry ether solvent. A catalyst such as a crystal of iodine may be added. The reaction was considered complete when no magnesium metal remained visible in the reaction mixture.

The reaction of the Grignard IX made from VIII with compound VII (the bromo-magnesium salt of VI) in the presence of dilithium tetrachlorocuprate in tetrahydrofuran gave X after hydrolysis of the reaction product such as with a mineral acid such as $H_2SO_4$. Preferably, compound VII in an ether solvent was combined with the lithium tetrachlorocuprate at a cool temperature, i.e., from about −30° C. to about 20° C. Upon further cooling, i.e., from about −30° C. to about 20° C., compound IX can be incrementally added with vigorous agitation over a period of time sufficient to allow maintenance of the low temperature. The reaction is conducted by stirring at the low temperature i.e., from about −20° C. to about 30° C. and then at an elevated temperature, i.e. from about 10° C. to about 40° C.

Baer and Carney disclosed coupling a saturated organic acid with a Grignard using dilithium tetrachlorocuprate (Baer, T. et al., *Tetrahedron Letters*, 1976, 4697).

The yield of unpurified X varied from 91–100% based on various preparative repeats. Recrystallization gave high purity X suitable for high resolution resists by electron beam microlithography. The overall yield of the raction base on the undecenyl alcohol was 83–91% and based on the raw material used to prepare compound VI (cyclododecanone) was 55–61%. These results are to be compared with prior overall yields of 8% (Stenhagen, E. *Arkiv Kemi, Min. O. Geol.*, 1949, 1, (13), 99) and 35% (Barraud, A. et al., *J. Colloid Interface Sci.*, 1977, 62, 509). Baer and Carney, *Tetrahedron Letters*, 1976, 4697, mention the formation of small amounts of diacid from homogeneous coupling of the omega-bromo acid. In this case, 1,24-tetracosadioic acid would be formed; none was noted by gas chromatography-mass spectroscopy analysis of the product of the present invention. It was found that traces of copper could be removed by washing with an aqueous solution of EDTA and citric acid. The product was also free of magnesium, sodium and lithium ions. The absence of metal ions is important for the production of photoresists.

The reaction conditions are given as exemplary for the specific reactions set forth in equations 5–8 and are not intended to be limiting to all of the reactants encompassed in the invention. Depending on the chain length, reactivity may vary requiring slight adjustment in reaction temperatures and reaction times. Based on the disclosure herein, these reaction variables can be easily determined by one of ordinary skill in the art.

The present invention will be further illustrated in the Example which follows:

EXAMPLE

PREPARATION OF 11-BROMODODECANOIC ACID (VI)

Cyclododecanone was treated with trifluoroacetic acid to form the lactone (Huisgen, R. et al., ibid), dodecanolid (yield 75%; bp 111°–115° C. at 8 mm). The lactone was hydrolyzed to form 12-hydroxydodecanoic acid (Smissman, E. et al., ibid) (yield 92%; mp 82°–4° C.). The hydroxy acid was converted to 12-bromododecanoic acid (VI) with 48% HBr in the presence of $H_2SO_4$ (Jocelyn, P. et al., ibid) (yield 88%; mp 52°–55° C.).

PREPARATION OF VII

A solution of 25 g (90 mmol) of VI in 100 mL dry THF was reacted under $N_2$ with 32.3 mL of 2.85M EtMgBr in $Et_2O$ added over a period of 30 minutes at 0° C. until there was no further evolution of gas.

PREPARATION OF 10-UNDECENYL CHLORIDE (VIII)

To a solution of 100 g (0.588 mole) of 10-undecenyl alcohol and 2 g of pyridine was added 75 g (0.63 mole) of $SOCl_2$ dropwise over a period of 45 minutes at 25° C. The solution was heated at 65° C. for 5 hours. $CH_2Cl_2$ (100 mL) was added and the solution was water washed twice, dried with $MgSO_4$, filtered, and the $CH_2Cl_2$ evaporated. The residue (103 g) by GC analysis showed a purity of 99.3% VIII with 0.7% alcohol; IR showed no OH band and absorbence at $1641^{-1}$. Distillation (15.24 centimeter jacketed Vigreaux column) gave 94 g VIII (bp 104°–105° C. at 6 mm) (GC showed no alcohol; 100% VIII).

PREPARATION OF IX

A well dried and $N_2$ flushed flask was charged with 2.2 g Mg ribbon (92 mmol), 80 mL dry THF, 16.1 g (92 mmol) VII and a small crystal of $I_2$. The mixture was stirred at reflux for 2 hours until no Mg was left. The reaction solution was used in the Reaction of VII and IX.

PREPARATION OF 22-TRICOSENOIC ACID (X) BY THE REACTION OF VII AND IX

To the THF solution of VII was added 9 mL of a 0.2M solution of $Li_2CuCl_4$ in THF (1.8 mmol) at $-10°$ C. The solution was cooled to $-20°$ C. and stirred vigorously while the solution of IX was added over a period of 45 minutes. After 1.5 hours stirring at $-20°$ C. and then 2 hours at 25° C., 125 mL of 10% $H_2SO_4$ was added to the dark blue reaction mixture. The white solid present in the reaction mixture went into solution. The reaction mixture was extracted with 100 mL toluene twice. The combined toluene extracts were washed with 5% $H_2SO_4$, dried over $MgSO_4$ and then flash distilled to give 29-32 g (91-100% yield; mp 68°–71° C.; MS showed no detectable $HO_2C(CH_2)_{24}CO_2H$ or any other mass $>C_{23}$; NMR showed no detectable $CH_3$; IR showed only $CH=CH_2$ unsaturation). Recrystallization from hexane solution washed with an aqueous solution of EDTA and citric acid gave white platelets, mp 73°–74° C. (97 mole % purity by DSC). High vacuum drying ($<1.0$ mm) gave mp 74.5° C. (99 mole % purity, DSC) (literature mp 73.5°–74° C., 74.3°–74.5° C., 75° C.; Barraud, A. et al. *J. Colloid Interface Sci.*, ibid; Stenhagen, E., ibid). X-ray fluorescence showed no detectable Na, Li, Mg, K, Cu, Br or I. A second recrystallization did not alter the 74.5° C. mp.

What is claimed is:

1. A method for preparing omega-unsaturated carboxylic acids of the formula:

$$CH_2=CH(CH_2)_{n1+n2}CO_2H$$

which comprises reacting a compound of the formula:

$$Halo^1(CH_2)_{n1}CO_2MgHalo^2$$

with a compound of the formula:

$$CH_2=CH(CH_2)_{n2}MgHalo^3$$

in an ether solvent in the presence of a catalyst of the formula $Li_2Cu(Halo^4)_4$, wherein $Halo^4$ can be chlorine or bromine, with acidic hydrolysis of the resulting product to form a compound of the first formula, wherein $Halo^1$, $Halo^2$ and $Halo^3$ are selected from the group consisting of chlorine, bromine and iodine, $n_1$ is an integer ranging from 4 to 20, and $n_2$ is an integer ranging from 3 to 20.

2. The method as recited in claim 1 wherein $Halo^1$ and $Halo^2$ are bromine.

3. The method of claim 1 wherein $Halo^3$ and $Halo^4$ are chlorine.

4. The method as recited in claim 1 which includes the further steps of preparing the compound of formula II by a process comprising the steps of reacting a compound of the formula:

$$Halo^1(CH_2)_{n1}CO_2H \qquad I$$

with a lower alkyl magnesium halide of $C_1$ to $C_4$ carbons of the formula $C_1$–$C_4MgHalo^2$ in the presence of an ether solvent to obtain the compound of formula II $Halo^1(CH_2)_{n1}CO_2MgHalo^2$.

5. The method as recited in claim 1 which includes the further steps of preparing the compound of formula IV by a process which comprises reacting a compound of the formula:

$$CH_2=CH(CH_2)_{n2}OH$$

with thionyl chloride to form a compound of the formula:

$$CH_2=CH(CH_2)_{n2}Halo^3 \qquad III$$

followed by reacting the compound of formula III with magnesium metal to form the compound of the formula IV $CH_2=CH(CH_2)_{n2}MgHalo^3$.

6. The method as recited in claim 4 wherein $Halo^1$ and $Halo^2$ are bromine.

7. The method as recited in claim 4 wherein said $C_1$–$C_4MgHalo^2$ is $C_1$–$C_2MgBr$.

8. The method as recited in claim 5 wherein said reaction of the compound of the formula:

$$CH_2=CH(CH_2)_{n2}OH$$

with thionyl chloride is conducted in the presence of a catalytic amount of a tertiary amine catalyst.

9. The method as recited in claim 5 wherein the reaction with magnesium metal is conducted in an ether solvent.

10. A method for preparing omega-unsaturated carboxylic acids of formula V $CH_2=CH(CH_2)_{n1+n2}CO_2H$ which comprises:
   (a) reacting a compound of formula I $Halo^1(CH_2)_{n1}CO_2H$ with a lower alkyl magnesium halide of the formula $C_1$–$C_4MgHalo^2$ in the presence of an ether solvent to obtain a compound of formula II $Halo^1(CH_2)_{n1}CO_2MgHalo^2$;
   (b) reacting a compound of the formula:

$$CH_2=CH(CH_2)_{n2}OH$$

with thionyl chloride in the presence of a catalytic amount of a tertiary amine to form a compound of formula III $CH_2=CH(CH_2)_{n2}Halo^3$ reacting the compound of formula III with magnesium metal to form a compound of formula IV $CH_2=CH(CH_2)_{n2}MgHalo^3$; and
   (c) reacting the compound of formula IV with the compound of formula II in an ether solvent in the presence of a catalytic amount of a compound of the formula $Li_2Cu(Halo^4)_4$ to form a compound of formula V, wherein $Halo^1$ and $Halo^2$ are halogen selected from the group of bromine, and iodine; $Halo^3$ and $Halo^4$ are halogen selected from the group of chlorine and bromine, $n_1$ is an integer of from 4 to 20; and $n_2$ is an integer of from 3 to 20.

11. The method as recited in claim 10 wherein $Halo^1$ and $Halo^2$ are bromine.

12. The method of claim 10 wherein $Halo^3$ and $Halo^4$ are chlorine.

13. The method as recited in claim 10 wherein said reaction is conducted in an ether solution.

14. The method as recited in claim 10 wherein $n_1$ is an integer ranging from 8 to 14 and $n_2$ is an integer ranging from 7 to 14.

15. The method as recited in claim 10 wherein said $C_1$–$C_4MgHalo^2$ is $C_1$–$C_2MgBr$.

* * * * *